United States Patent
Ohishi (10) Patent No.: US 11,058,357 B2
(45) Date of Patent: Jul. 13, 2021

(54) ACOUSTIC WAVE APPARATUS AND CONTROL METHOD THEREOF

(71) Applicant: CANON KABUSHIKI KAISHA, Tokyo (JP)

(72) Inventor: Shinji Ohishi, Oyama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 820 days.

(21) Appl. No.: 15/629,351

(22) Filed: Jun. 21, 2017

(65) Prior Publication Data

US 2017/0367656 A1 Dec. 28, 2017

(30) Foreign Application Priority Data

Jun. 28, 2016 (JP) .............................. JP2016-127473

(51) Int. Cl.
*A61B 5/00* (2006.01)
*A61B 8/00* (2006.01)
(Continued)

(52) U.S. Cl.
CPC .............. *A61B 5/70* (2013.01); *A61B 5/0095* (2013.01); *A61B 5/708* (2013.01); *A61B 8/14* (2013.01);
(Continued)

(58) Field of Classification Search
None
See application file for complete search history.

(56) References Cited

U.S. PATENT DOCUMENTS

| 4,282,880 A | * | 8/1981 | Gardineer | A61B 8/0825 |
| | | | | 128/915 |
| 6,778,848 B1 | | 8/2004 | Bechtold et al. | |

(Continued)

FOREIGN PATENT DOCUMENTS

| CN | 1596823 A | 3/2005 |
| CN | 102525554 A | 7/2012 |

(Continued)

OTHER PUBLICATIONS

Office Action dated Jun. 3, 2020, in counterpart application CN 201710483632.1 (22 pages).

(Continued)

*Primary Examiner* — Luther Behringer
*Assistant Examiner* — Farouk A Bruce
(74) *Attorney, Agent, or Firm* — Venable LLP (57) ABSTRACT

An acoustic wave apparatus is used, the apparatus comprising: a supporting member supporting an examinee and having insertion opening; a subject holding member holding the subject; a transducer array including transducers and being distant from the subject holding member; a load acquiring unit acquiring a load value applied between the supporting member and the subject holding member based on an amount of deformation of the subject holding member; a memory unit storing a first load reference value determined based on the amount of deformation of the subject holding member and an area applied with the load when the subject holding member and the transducer array come into contact with each other; a comparing and determining; and an interlock controlling unit.

25 Claims, 7 Drawing Sheets

(51) Int. Cl.
*A61B 8/14* (2006.01)
*A61B 8/08* (2006.01)

(52) U.S. Cl.
CPC ............... *A61B 8/40* (2013.01); *A61B 8/406* (2013.01); *A61B 8/4281* (2013.01); *A61B 8/54* (2013.01); *A61B 8/0825* (2013.01)

(56) References Cited

U.S. PATENT DOCUMENTS

| | | | |
|---|---|---|---|
| 10,105,061 B2 | 10/2018 | Tanaka et al. | |
| 10,499,815 B2 | 12/2019 | Nishihara et al. | |
| 2004/0064046 A1* | 4/2004 | Shehada | A61B 8/483 600/437 |
| 2009/0262887 A1* | 10/2009 | Iordache | A61B 6/025 378/37 |
| 2011/0049372 A1* | 3/2011 | Iseki | A61N 5/1043 250/362 |
| 2012/0136234 A1 | 5/2012 | Taku | |
| 2012/0238858 A1* | 9/2012 | Tokita | A61B 5/0095 600/407 |
| 2015/0031998 A1* | 1/2015 | Kyono | A61B 8/4281 600/437 |
| 2015/0119680 A1 | 4/2015 | Tanaka et al. | |
| 2015/0119683 A1* | 4/2015 | Kyono | A61B 5/704 600/407 |
| 2015/0119714 A1 | 4/2015 | Nakabayashi et al. | |
| 2016/0069837 A1 | 3/2016 | Nakabayashi et al. | |
| 2016/0166217 A1* | 6/2016 | Davis | A61B 6/025 378/37 |
| 2016/0174849 A1 | 6/2016 | Nanaumi et al. | |
| 2017/0035361 A1 | 2/2017 | Yamamoto | |
| 2017/0224223 A1 | 8/2017 | Nishihara et al. | |

FOREIGN PATENT DOCUMENTS

| | | |
|---|---|---|
| CN | 104586353 A | 5/2015 |
| CN | 105395165 A | 3/2016 |
| DE | 102013208794 A1 | 11/2014 |
| JP | 2009-28381 A | 2/2009 |
| JP | 2015-167733 A | 9/2015 |
| JP | 2015-205041 A | 11/2015 |
| JP | 2016-2373 A | 1/2016 |
| JP | 2017-522994 A | 8/2017 |
| JP | 2018-82743 A | 5/2018 |
| WO | 2016/035343 A1 | 3/2016 |

OTHER PUBLICATIONS

Notice of Allowance dated Sep. 17, 2020, in counterpart application in KR 10-2017-0079413 (3 pages).
Office Action dated Jan. 18, 2021 in counterpart application CN 201710483632.1 (12 pages).

* cited by examiner

ACOUSTIC WAVE APPARATUS AND CONTROL METHOD THEREOF

BACKGROUND OF THE INVENTION

Field of the Invention

The present invention relates to an acoustic wav apparatus and a control method thereof.

Description of the Related Art

Research on acoustic wave imaging apparatuses (acoustic wave apparatus) which cause pulsed light irradiated on a subject from a light source to propagate inside the subject to obtain information inside the subject is being aggressively promoted mainly in the field of medicine. Photoacoustic tomography (PAT) is proposed as one of such acoustic wave imaging techniques. PAT is a technique for visualizing information related to optical characteristics inside a subject. To this end, an acoustic wave imaging apparatus using PAT irradiates a subject with pulsed light generated from a light source. In addition, the acoustic wave imaging apparatus receives an acoustic wave (typically, an ultrasound wave) generated when light having been propagated and disseminated inside the subject is absorbed by body tissue with a transducer and subjects the received acoustic wave to an analysis process.

An acoustic wave in a frequency band of several MHz to over 10 MHz is used to diagnose body tissue. The acoustic wave attenuates in the course of propagating inside a living organism. The higher the frequency, the greater the degree of attenuation of the acoustic wave. An occurrence of a significant attenuation causes image quality in a deep portion (a portion relatively distant from a transducer) of the living organism to decline and affects diagnostic performance. In consideration thereof, a technique is known which, in an acoustic wave imaging apparatus, a subject is held by a sheet-like holding member and an acoustic wave from the subject is acquired via the holding member.

Japanese Patent Application Laid-open No. 2015-167733 discloses an acoustic wave imaging apparatus which holds a subject with a holding member in contact with a receiving surface of an ultrasound transducer and the subject. Japanese Patent Application Laid-open No. 2015-167733 further discloses suppressing a decline in an S/N ratio of an acquired ultrasound signal by using a mesh-like holding member with respect to multiple reflection of ultrasound waves caused by an interface formed by a sheet-like holding member. Japanese Patent Application Laid-open No. 2015-167733

SUMMARY OF THE INVENTION

When a subject is held by a mesh-like holding member as described above, a load value equal to or exceeding an expected value may possibly be applied to the mesh-like holding member due to the effect of a body motion (for example, a change in posture) of the subject. In some cases, the mesh-like holding member deformed by the load value comes into contact with peripheral members such as a transducer arranged in a periphery of the holding member and damages the holding member or the transducer. This problem requires improvement since both damage to the holding member and damage to the transducer result in destabilizing reception characteristics.

The present invention has been made in consideration of the problems described above. An object of the present invention is to reduce the effect of deflection of a subject holding member in an acoustic wave imaging apparatus.

The present invention provides acoustic wave apparatus, comprising:

a supporting member configured to support an examinee, and provided with an insertion opening through which the subject is configured to be inserted;

a subject holding member configured to hold the subject inserted though the insertion opening;

a transducer array configured to include a plurality of transducers for receiving acoustic waves and configured to be distant from the subject holding member;

a load acquiring unit configured to acquire a load value applied between the supporting member and the subject holding member based on an amount of deformation of the subject holding member;

a memory unit configured to store a first load reference value determined based on the amount of deformation of the subject holding member and an area applied with the load when the subject holding member and the transducer array come into contact with each other;

a comparing and determining unit configured to compare the load value with the first load reference value; and an interlock controlling unit configured to perform interlock control when the comparing and determining unit determines that the load value exceeds the first load reference value.

The present invention also provides a control method of an acoustic wave apparatus including: a supporting member configured to support an examinee and provide with an insertion opening through which the subject configured to be inserted; a subject holding member configured to hold the subject; a transducer array including a plurality of transducers and configured to be distant from the subject holding member; a load acquiring unit; a comparing and determining unit; and an interlock controlling unit, the method comprising:

receiving, by the transducer, an acoustic wave generated from the subject and output an electrical signal;

acquiring, by the load acquiring unit, a load value corresponding to an amount of deformation of the subject holding member due to a load of the subject;

comparing, by the comparing and determining unit, the load value with a first load reference value which is determined based on the load value when the subject holding member and the transducer array come into contact with each other; and performing, by the interlock controlling unit, interlock control when the comparing and determining unit determines that the load value exceeds the first load reference value.

According to the present invention, the effect of deflection of a subject holding member in an acoustic wave apparatus can be reduced.

Further features of the present invention will become apparent from the following description of exemplary embodiments with reference to the attached drawings.

DESCRIPTION OF THE EMBODIMENTS

Hereinafter, preferred embodiments of the present invention will be described with reference to the drawings. However, it is to be understood that dimensions, materials, shapes, relative arrangements, and the like of components described below are intended to be changed as deemed appropriate in accordance with configurations and various conditions of apparatuses to which the present invention is to be applied. Therefore, the scope of the present invention is not intended to be limited to the embodiments described below.

The present invention relates to a technique for detecting an acoustic wave propagating from a subject and generating and acquiring specific information on the inside of the subject. Accordingly, the present invention can be considered a subject information acquiring apparatus or a control method thereof, or a subject information acquiring method and a signal processing method. The present invention can also be considered a program that causes an information processing apparatus including hardware resources such as a CPU and a memory to execute these methods or a computer-readable non-transitory storage medium storing the program.

The subject information acquiring apparatus according to the present invention includes an apparatus utilizing a photoacoustic effect in which an acoustic wave generated inside a subject by irradiating the subject with light (an electromagnetic wave) is received and characteristic information on the subject is acquired as image data. In this case, characteristic information refers to information on a characteristic value corresponding to each of a plurality of positions inside the subject which is generated using a received signal obtained by receiving a photoacoustic wave.

Characteristic information (photoacoustic characteristic information) derived from an electrical signal (a photoacoustic signal) acquired by photoacoustic measurement is a value reflecting an absorption rate of optical energy. For example, characteristic information includes a generation source of an acoustic wave generated by light irradiation, initial sound pressure inside a subject, light energy absorption density or an absorption coefficient derived from initial sound pressure, and a concentration of substances constituting tissue. In addition, a distribution of oxygen saturation can be calculated by obtaining a concentration of oxygenated hemoglobin and a concentration of deoxygenated hemoglobin as concentrations of substances. Furthermore, a glucose concentration, a collagen concentration, a melanin concentration, a volume fraction of fat or water, and the like can also be obtained.

The subject information acquiring apparatus according to the present invention includes an apparatus using ultrasound echo technology which transmits an ultrasound wave to a subject, receives a reflected wave (an echo wave) that is reflected inside the subject, and acquires subject information as image data. Characteristic information (ultrasound characteristic information) derived from an electrical signal (an ultrasound echo signal) acquired by an ultrasound echo apparatus is information reflecting a difference in acoustic impedances among tissues inside a subject.

A two-dimensional or three-dimensional characteristic information distribution is obtained based on characteristic information at each position in the subject. Distribution data may be generated as image data. Characteristic information may be obtained as distribution information at respective positions inside the subject instead of as numerical data. Examples of distribution information include a distribution of initial sound pressure, a distribution of energy absorption density, a distribution of absorption coefficients, a distribution of oxygen saturation, a distribution of acoustic impedance, and distribution information representing blood flow. Since information based on an acoustic wave is visualized as described above, the present invention can also be considered an acoustic wave imaging apparatus, a control method of an acoustic wave imaging apparatus, or a program of an acoustic wave imaging apparatus. Moreover, the present invention can also be considered just as an acoustic wave apparatus and control method thereof.

An acoustic wave as referred to in the present invention is typically an ultrasound wave and includes an elastic wave which is also referred to as a sound wave or an acoustic wave. An electrical signal transformed from an acoustic wave by a transducer is also referred to as an acoustic signal. However, descriptions of an ultrasound wave and an acoustic wave in the present specification are not intended to limit a wavelength of such elastic waves. An acoustic wave generated by a photoacoustic effect is referred to as a photoacoustic wave or an optical ultrasound wave. An electrical signal derived from a photoacoustic wave is also referred to as a photoacoustic signal. In addition, an electrical signal derived from an echo wave applied when a transmission ultrasound wave is reflected by a subject is also referred to as an ultrasound echo signal.

First Embodiment

Hereinafter, a first embodiment of the present invention will be described with reference to the drawings. It should be noted that same components are generally assigned same reference numerals and a description thereof will be omitted. The present embodiment will be described using an example of a photoacoustic imaging apparatus as an acoustic wave imaging apparatus according to the present embodiment. However, as described above, the present invention is also applicable to ultrasound echo imaging. Furthermore, the present invention is also applicable to other inspection apparatuses. In particular, the present invention is preferably applied to an inspection apparatus adopting a system in which a breast in a held state is measured by a probe or a sensor.

Apparatus Configuration

Figure 1:
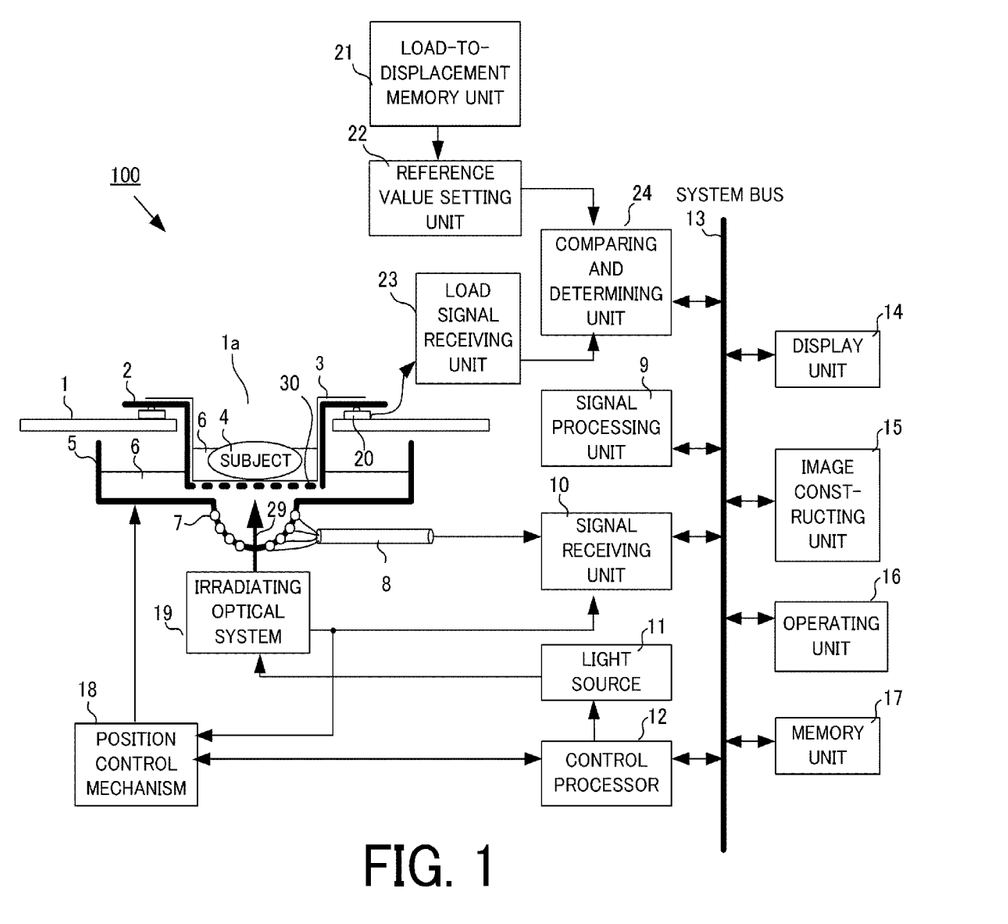
FIG. 1 is a block diagram of an acoustic wave imaging apparatus according to a first embodiment.

FIG. 1 is a block diagram showing an acoustic wave imaging apparatus 100 (hereinafter, also simply referred to as the "apparatus 100") according to the present embodiment. The apparatus 100 includes the following. A subject 4 is held by a subject holding member 2 constituted by a mesh member 30 provided with an opening (gap) and a waterproof sheet member 3. The apparatus 100 includes a plurality of transducers 7 for receiving a photoacoustic wave propagating from the subject 4 and a position control mechanism 18 for controlling relative positions of the subject 4 and the transducers 7.

The apparatus 100 further includes a light source 11 which generates light and an irradiating optical system 19 which irradiates the subject 4 with the light. An electrical signal (a photoacoustic signal) output from the transducers 7 is a weak high-frequency analog signal which is transmitted to a signal receiving unit 10 via a coaxial cable 8. The signal receiving unit 10 amplifies and performs A/D conversion on the photoacoustic signal, and outputs a photoacoustic digital signal to a signal processing unit 9. The signal processing unit 9 is assumed to perform an integrating process of photoacoustic digital signals to generate subject information.

The apparatus 100 further includes an operating unit 16 used by a user (a medical worker including an operating engineer and a radiographer) to input instructions including an instruction to start imaging and parameters necessary for imaging to the apparatus 100, and an image constructing unit 15 which converts subject information acquired by a generating unit into an image. In addition, a display unit 14 displaying a user interface (UI) for displaying a generated image or operating the apparatus is also provided.

The apparatus 100 further includes a control processor 12 which accepts various operations by the user via the operating unit 16, generates control information necessary for generating desired subject information, and controls respective functions via a system bus 13. In addition, a memory unit 17 which stores acquired photoacoustic digital signals, generated images, and other information related to operations is provided. Moreover, the subject 4 which is an imaging subject is, for example, a breast in breast cancer diagnosis at a breast oncology department and a hand or a foot in vascular diagnosis at a department of dermatology or an orthopedic department. In addition, an organism such as a mouse or a frog, a phantom simulating a living specimen, and the like may also be used as a measurement subject. Hereinafter, the respective components of the apparatus 100 will be described in detail.

<<Object Holding Member 2>>

The mesh member 30 is arranged on a lower surface of the subject holding member 2 in order to both support a weight of the subject 4 and increase transmittivity of an acoustic wave and suppress multiple reflection. An article made by knitting fiber can be used as the mesh member 30. In order to reduce attenuation of an acoustic wave, a diameter of the fiber is favorably shorter than a wavelength of the acoustic wave. The diameter of the fiber is, for example, 0.01 mm to 0.5 mm. A ratio of the fiber to an insertion opening of a reticulated member is favorably minimal. The ratio of the fiber to the insertion opening is, for example, 60% or lower. Moreover, from the perspective of improving comfortability, a structure which prevents the mesh member 30 from coming into contact with the subject is favorable. However, depending on a material of the mesh member 30, the mesh member 30 may be brought into contact with the subject. In addition, as long as transmittivity of an acoustic wave can be secured, the mesh member 30 may be sandwiched by the waterproof sheet member 3.

In order to support weights of the subject and an acoustic matching liquid, the mesh member 30 is favorably a material with high tensile strength and a low elastic deformation rate. Examples of preferable materials include polyethylene terephthalate, polyarylate, and polyester. Using a material with high tensile strength as the mesh member 30 enables the subject to be held in an approximately flat shape. As a result, since an acoustic wave from deep portions of the subject can be received, favorable diagnostics can be performed. By knitting the mesh member 30 in a lattice shape discretely having openings (gaps) between the fibers, a vertical reflection component of an acoustic wave is reduced as compared to a planar member with no openings (gaps). As a result, multiple reflection of an acoustic wave is reduced. The lattice-shaped fibers may be knitted by a method in which a shape of the openings (gaps) are rectangular as well as a method in which the openings (gaps) are hexagonal or octagonal. However, since the subject holding member 2 according to the present invention is expected to become deflected or the like, a material which allows a certain amount of deformation is favorable.

In addition, in order to immerse the subject 4 in an acoustic matching liquid 6 to match acoustic impedances between the subject 4 and the transducers, the thin rubber-shaped waterproof sheet member 3 is arranged in the subject holding member 2. The waterproof sheet member 3 is constituted by isoprene (IR) rubber which is structurally similar to natural rubber. In order to prevent the waterproof sheet member 3 from bending and floating, the waterproof sheet member 3 and the mesh member 30 are favorably fixed to each other. Examples of fixing methods include fixing by an adhesive, welding, and clamping by a member. However, in order to prevent attenuation or reflection of an acoustic wave due to a fixing interface or a fixing member, fixing is favorably performed in a peripheral section of each member or outside of an imaging region.

The waterproof sheet member 3 holds the acoustic matching liquid 6 in a watertight manner. In order to reduce attenuation of an acoustic wave when the acoustic wave is being transmitted through the waterproof sheet member 3, the waterproof sheet member 3 is favorably thin. More favorably, the thickness of the waterproof sheet member 3 is shorter than a wavelength of a used acoustic wave. For example, the thickness of the waterproof sheet member is set within a range of 0.01 mm to 1 mm. In addition, in order to increase adhesion to the subject, the waterproof sheet member 3 is favorably made of a stretchable elastic material. Other than natural rubber and IR rubber, examples of such a material include polymethylpentene, polyethylene terephthalate, polyester, and silicone rubber.

The subject holding member 2 is held by the supporting member 1 via a load detector 20 including a load cell. As described above, since the subject holding member 2 has a function of holding the subject 4 that is an imaging subject as well as a function of a container for holding a certain amount of the acoustic matching liquid 6, the subject holding member 2 is also referred to as an imaging tub. In order to insert the subject 4, the subject holding member has a container shape with an opening or, in other words, a semi-container shape. The supporting member 1 has an insertion opening 1a for inserting a subject which constitutes a part of an examinee. The supporting member 1 is strong enough to support a weight of the examinee and has a supporting surface including a planar section. A case capable of internally storing various components is preferable as the supporting member 1.

<<Transducer Array 5>>

The transducer array 5 includes a hemispherically-shaped (or bowl-shaped or cup-shaped) supporter. In order to efficiently receive a photoacoustic wave from the subject 4, a plurality of transducers 7 are arranged on the supporter in a concentric pattern or a spiral pattern. Moreover, the transducers 7 may be arranged one-dimensionally (linearly) or two-dimensionally (planarly). The transducer array is arranged inside the supporting member (case) below the subject and the subject holding member at a distance there-from. The distance between the transducer array and the holding member is favorably equal to or greater than a permissible gap g.

In order to reduce attenuation of an acoustic wave from the subject 4, the transducer array 5 is filled with the acoustic matching liquid 6 in a similar manner to the subject holding member 2. In order to hold the acoustic matching liquid 6, a flange with an open upper part and a semi-container shape and a wall are connected in a periphery of the hemispherically-shaped supporter. The position control mechanism 18 one-dimensionally or two-dimensionally scans the transducer array 5 and controls relative positions of the transducer array 5 and the subject holding member 2.

<<Position Control Mechanism 18>>

The position control mechanism 18 is constituted by a drive member including a motor and a mechanical part for transmitting a driving force thereof, and controls a position of the transducer array 5 in accordance with scan control information from the control processor 12. By repetitively performing irradiation of pulsed light 29 and acquisition of a photoacoustic wave while changing relative positions of the transducers 7 attached to the transducer array 5 with respect to the subject 4, desired subject information over a wide range can be acquired. In addition, in synchronization with control of one emission of the pulsed light 29 by the irradiating optical system 19, the position control mechanism 18 outputs present position control information to the control processor 12. The position control mechanism corresponds to the position control unit according to the present invention.

<<Light Source 11>>

The light source 11 emits pulsed light (with a width of 100 nm or less) having a central wavelength in a near infrared range. As the light source 11, generally, a solid state laser (for example, an Yttrium-Aluminum-Garnet laser or a Titanium-Sapphire laser) capable of emitting pulsed light having a central wavelength in a near infrared range is used. Lasers such as a gas laser, a dye laser, and a semiconductor laser can also be used. Alternatively, a flash lamp or a light-emitting diode can be used.

Moreover, the wavelength of light is selected in accordance with light-absorbing substances (for example, oxygenated hemoglobin or deoxygenated hemoglobin, a blood vessel containing oxygenated hemoglobin or deoxygenated hemoglobin in large amounts, a malignant tumor containing a large amount of new blood vessels, glucose, and cholesterol) inside the living organism that is a measurement subject. Hereinafter, as an example, a case will be considered where hemoglobin flowing through a new blood vessel positioned so as to overlap with breast cancer is selected as a measurement subject. Hemoglobin generally absorbs light in a range of 600 to 1000 nm. On the other hand, light absorption by water constituting the living organism is approximately minimized around 830 nm. Therefore, light absorption by hemoglobin relatively increases from 750 to 850 nm. In addition, the absorption rate of light changes for each wavelength of light in accordance with oxygen saturation of hemoglobin. In consideration thereof, a functional change in the living organism can also be measured using a distribution of absorbance of hemoglobin and dependency of oxygen saturation of an absorbance spectrum.

<<Irradiating Optical System 19>>

The irradiating optical system 19 guides pulsed light emitted by the light source 11 toward the subject and forms and emits light 29 suitable for signal acquisition. The irradiating optical system 19 is typically constituted by optical parts such as a lens or a prism which collects or magnifies light, a mirror which reflects light, and a diffuser plate which disseminates light. In addition, an optical fiber, an optical waveguide, or the like can be used to guide light from the light source 11 to the irradiating optical system 19. Moreover, generally, as living organism protection criteria regarding irradiation light with respect to skin and eyes, a maximum permissible exposure is defined by IEC 60825-1 in accordance with conditions such as a wavelength of light, duration of exposure, and pulse repetition. The irradiating optical system 19 generates the light 29 satisfying the same criteria with respect to the subject 4.

Furthermore, the irradiating optical system 19 includes an optical component (not shown) which detects emission of the light 29 to the subject 4 and, in synchronization therewith, generates a synchronization signal for controlling reception and recording of a photoacoustic signal. By dividing, with an optical system such as a half mirror, a part of the pulsed light generated by the light source 11 to guide the divided light to an optical sensor, the emission of the light 29 toward the subject 4 can be detected using a detected signal generated by the optical sensor based on the guided light. When a bundle fiber is used to guide the pulsed light, emission of light can be detected by bifurcating a part of the fiber and guiding the light to the optical sensor with the bifurcated part. The synchronization signal generated due to detection of emission of the light 29 is input to the signal receiving unit 10 and the position control mechanism 18.

<<Signal Receiving Unit 10>>

In accordance with the synchronization signal input from the irradiating optical system 19, the signal receiving unit 10 amplifies a photoacoustic signal generated by the transducers 7 and converts the photoacoustic signal into a photoacoustic digital signal which is a digital signal. The signal receiving unit 10 is constituted by a signal amplifying unit which amplifies an analog signal generated by the transducers 7 and an A/D conversion unit which converts the analog signal into a digital signal.

<<Signal Processing Unit 9>>

The signal processing unit 9 subjects the photoacoustic digital signal generated by the signal receiving unit 10 to correction of a variation in sensitivity of the transducers 7, an interpolation process of a transducer with physical or electrical defects, and the like. In addition, the signal processing unit 9 is also capable of performing an integration process for noise reduction. A photoacoustic signal obtained by detecting a photoacoustic wave generated by a light-absorbing substance inside the subject 4 is generally a weak signal. In consideration thereof, by applying an integrating and averaging process to a photoacoustic signal repetitively acquired at a same position with respect to the subject 4, system noise can be reduced and S/N of the photoacoustic signal can be improved.

<<Control Processor 12>>

The control processor 12 executes the functions described below by running an operating system (OS) which, for instance, controls and manages basic resources in a program operation and reading a program code stored in a memory unit 17. In addition, the control processor 12 manages an acquisition operation of subject information upon receiving an event notification generated by various operations performed by a user via the operating unit 16 including start of imaging, and controls various pieces of hardware via the system bus 13. The control processor 12 further performs irradiation control of the light 29 and position control of the transducers 7 which are necessary for generating desired subject information. When the control processor performs an operation related to interlock control, the control processor corresponds to the interlock controlling unit according to the present invention.

<<Operating Unit 16>>

The operating unit 16 is an input apparatus used by the user to set parameters related to imaging including a visualization range of subject information, instruct start of imaging, perform image processing operations related to an image, and the like. Generally, the operating unit 16 is constituted by a mouse, a keyboard, a touch panel, or the like and performs an event notification with respect to software running on the control processor 12 in accordance with an operation by the user. In this case, software includes the operating system (OS).

<<Image Constructing Unit 15>>

Based on an acquired photoacoustic digital signal, the image constructing unit 15 images tissue information inside the subject and constructs a display image including an arbitrary tomographic image of a photoacoustic image. In addition, the image constructing unit 15 applies various correction processes such as brightness correction, distortion correction, and clipping-out of a region of interest to the constructed image to construct information more favorable for diagnosis. Furthermore, in accordance with a user operation via the operating unit 16, the image constructing unit 15 adjusts parameters related to the construction of a photoacoustic image, adjusts a display image, and the like.

A photoacoustic image is obtained by subjecting a digital signal of a three-dimensional photoacoustic wave generated by the transducers 7 to an image reconstruction process. Due to the image reconstruction process, subject information such as a distribution of characteristics including acoustic impedance and a distribution of optical characteristic values can be visualized. As the image reconstruction process, back projection in a time domain or a Fourier domain which is commonly used in tomographic technology, a phasing addition process, or the like can be used. Moreover, when time constraints are not stringent, an image reconstruction method including an inverse problem analysis method by repetitive processing can be used.

The use of a transducer equipped with a reception focusing function using an acoustic lens or the like enables subject information to be visualized without having to perform image reconstruction. The image constructing unit 15 is generally constituted by a graphics processing unit (GPU) or the like having a high-performance arithmetic processing function and a graphic display function. Accordingly, the time required by an image reconstruction process or construction of a display image can be reduced.

<<Display Unit 14>>

The display unit 14 displays a photoacoustic image constructed by the image constructing unit 15 and a UI for operating images and the apparatus. The display unit 14 may be a display based on any system such as a liquid crystal display and an organic electro luminescence (EL) display. Moreover, the display unit 14 may be provided as a part of the apparatus according to the present invention or may be provided separate from the apparatus. In the latter case, the apparatus according to the present invention outputs or stores image data.

<<Memory Unit 17>>

The memory unit 17 is constituted by storage media including a memory necessary for the control processor 12 to operate, a memory which temporarily holds data during a subject information acquisition operation, and a hard disk which, for instance, stores and holds a generated photoacoustic image, related subject information, and diagnostic information. In addition, the memory unit 17 stores a program code of software which realizes the functions described hereinafter.

Typically, the signal processing unit 9, the control processor 12, the image constructing unit 15, the memory unit 17, as well as a load-to-displacement memory unit 21, a reference value setting unit 22, a load signal receiving unit 23, a comparing and determining unit 24, and the like to be described later are implemented by an information processing apparatus. An apparatus (for example, a PC or a work station) which includes a CPU, a storage apparatus, a communication apparatus, and the like and which runs in accordance with a program stored in a non-transitory storage medium readable by the information processing apparatus is preferable as such an information processing apparatus. For example, the operating unit 16 is implemented by an input user interface of such an information processing apparatus. For example, the display unit 14 is implemented by a display connected to such an information processing apparatus.

(Consideration when Load is Applied)

Figure 2A:
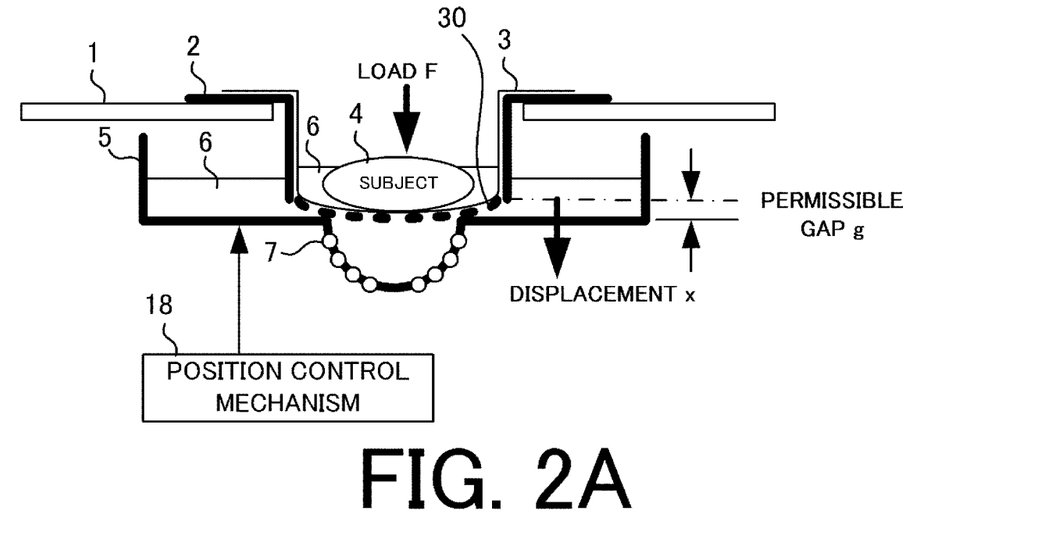
FIGS. 2A and 2B are diagrams illustrating a deflection of a subject holding member.

Phenomena which may occur in an acoustic wave imaging apparatus according to the present invention will now be considered with reference to FIG. 2. Arranging the mesh member 30 on a lower surface of the subject holding member 2 is effective in suppressing multiple reflection of an acoustic wave from the subject 4. However, the mesh shape may cause rigidity to be insufficient and, in some cases, the mesh member may become deflected when holding the subject 4. In particular, as shown in FIG. 2A, when a larger-than-expected measurement load F is applied due to a body motion of the subject 4 or the like, the mesh member 30 is displaced (by an amount of displacement x) from an initial position indicated by a dot chain line. Moreover, in this case, a position of a portion at a bottommost point of the mesh member in a z axis direction (an up-down direction of a paper plane) is used as a reference of the position of the mesh member. In FIG. 2A, the bottommost point of the mesh member is lower than the dot chain line.

To what degree deformation of the subject holding member 2 is to be permitted will be considered from the perspective of the subject holding member 2 coming into contact with members such as transducers. Typically, a lowest position (a bottommost point) of the subject holding member along the Z axis is favorably higher than a certain prescribed position even when under a load value due to a body motion or the like. This is also referred to as a bottommost point guarantee. Whether or not a bottommost point guarantee has been made can be determined based on whether or not a load value is lower than a reference value as described above. In addition, the determination can also be made based on whether or not an amount of leakage or a height of a liquid level of a matching liquid exceeds a prescribed value. Furthermore, the subject may be imaged by an optical camera or an ultrasound echo and the imaged subject may be analyzed. Alternatively, a bottommost point guarantee can be determined by any method.

Figure 2B:
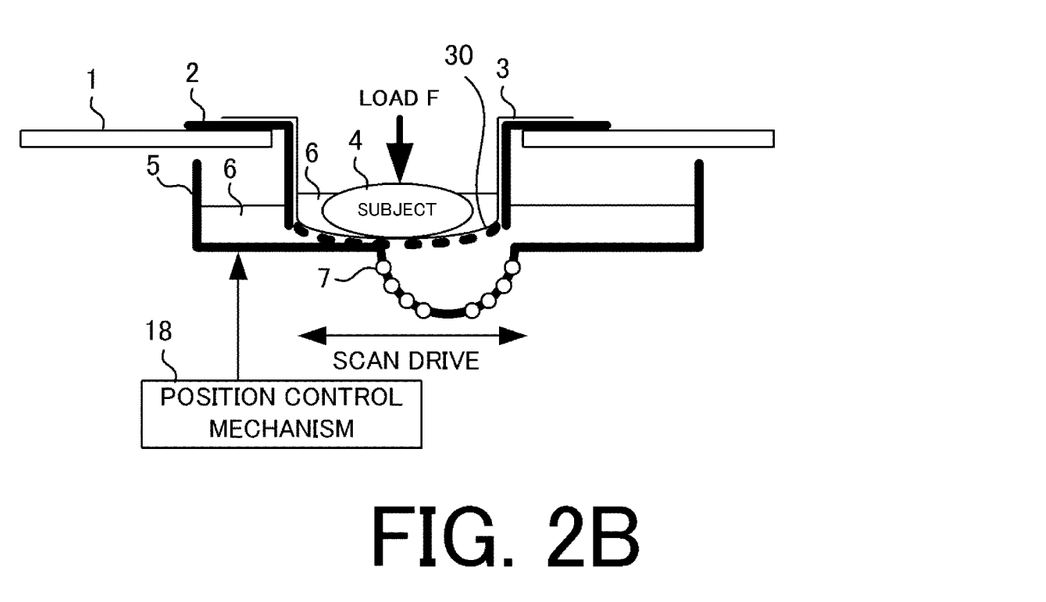

When the measurement load F from the subject 4 increases, the mesh member 30 may become deflected and come into contact with a bottom surface of the transducer array 5 as shown in FIG. 2B. Furthermore, a case where scan driving for imaging is started by the position control mechanism 18 in the contact state will be considered. For example, when the subject 4 is a human body part (a hand, a foot, a breast, or the like), there is a possibility that the subject 4 may come into contact with the transducer array 5 via the mesh member 30. Such a contact may result in damaging the mesh member 30 and the transducer array 5 and may cause accuracy of image data to decline due to a change in the characteristics of the subject 4 when pressed.

Such a contact can be prevented by increasing a distance (the permissible gap g) between the mesh member 30 arranged on the lower surface of the subject holding member 2 and a bottom surface of the transducer array 5. However, increasing the distance from the subject 4 to the transducers 7 may result in a lower signal strength and cause a decline in an S/N ratio of an image. In addition, an increased transducer array 5 which is three-dimensionally mounted with a plurality of transducers may be required in proportion with the permissible gap g, in which case the size of the apparatus increases.

In consideration thereof, as in FIG. 1, in the present embodiment, the load detector 20 measures a load F applied to the subject holding member 2 and transmits the measured load F to the load signal receiving unit 23. This load value is also referred to as a load strength signal. As the load detector 20, for example, a load cell can be used. In this case, prior to imaging, a relationship between the load F and the displacement x shown in FIG. 2A may be obtained in advance and a result thereof may be stored in the load-to-displacement memory unit 21. A reference value (a permissible value) of the load F is obtained based on the relationship between the load value and the displacement and a value is set to the comparing and determining unit 24 by the reference value setting unit 22.

The comparing and determining unit 24 compares the reference value and the load value with each other. When the load value exceeds the reference value, the comparing and determining unit 24 notifies the control processor 12 of a permissible load error signal or the like. In addition, a safety process including a driving stop measure is executed by the position control mechanism 18 before the mesh member 30 comes into contact with a part of the transducer array 5. Such a safety process is also referred to as interlock control. Various methods of performing interlock control are conceivable. For example, a method of stopping a scan or a method of retracting a member which may come into contact with the subject holding member are conceivable as a favorable interlock control method. In addition, a result of the comparison and determination is favorably presented to the user by a presenting unit such as a display or a speaker. Furthermore, light irradiation is favorably stopped. Moreover, signal reception and the like are also stopped in parallel with physical control.

(Details of Load Detecting Unit)

Figure 3:
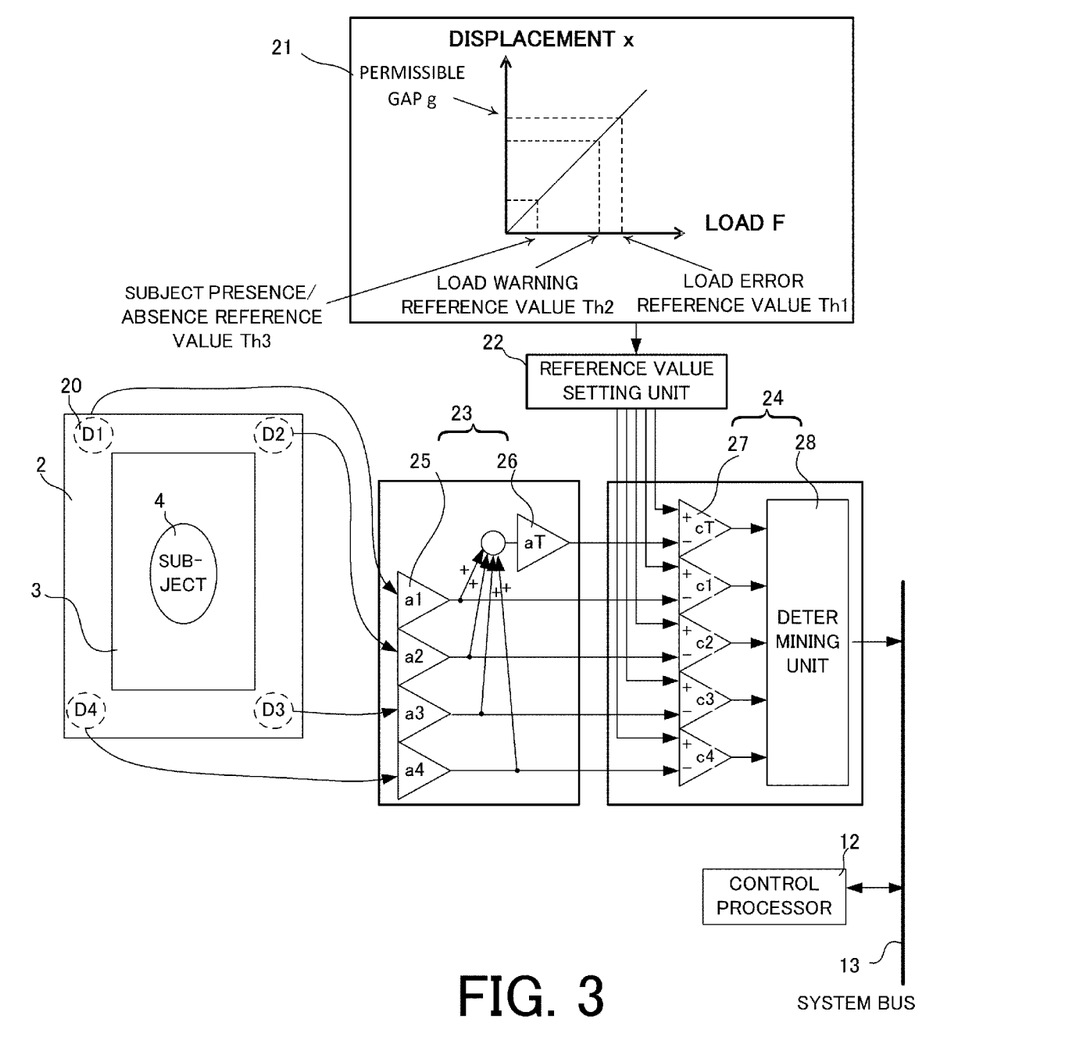
FIG. 3 is a block diagram of a load detecting unit of an acoustic wave imaging apparatus.

FIG. 3 shows a detailed block diagram of a load detecting unit. A left side of a lower part of the diagram shows the subject holding member 2 as viewed from above. The load detector 20 including a load cell is arranged at four corners of the subject holding member 2 (D1 to D4). At least one load detector 20 or more may suffice in order to detect a load. However, in order to measure a load value applied near a center of the subject holding member 2, a plurality of load transducers are favorably arranged on opposite sides of the subject 4.

A center of the lower part of the diagram corresponds to the load signal receiving unit 23. A signal from the load detector 20 is amplified by a transducer amplifier 25 (a1, a2, a3, and a4). By adding up respective amplified load values by an adder 26 (aT), a sum value of load values applied to the subject holding member 2 can be acquired. Alternatively, an averaging process may be performed instead of an adding process. In order to increase accuracy of measurement of the load value on the subject holding member 2 by the load detector 20, the subject holding member 2 is favorably held so as to be restrained in a horizontal direction but with a degree of freedom in a vertical direction while avoiding contact with the supporting member 1 and the like.

Figure 6:
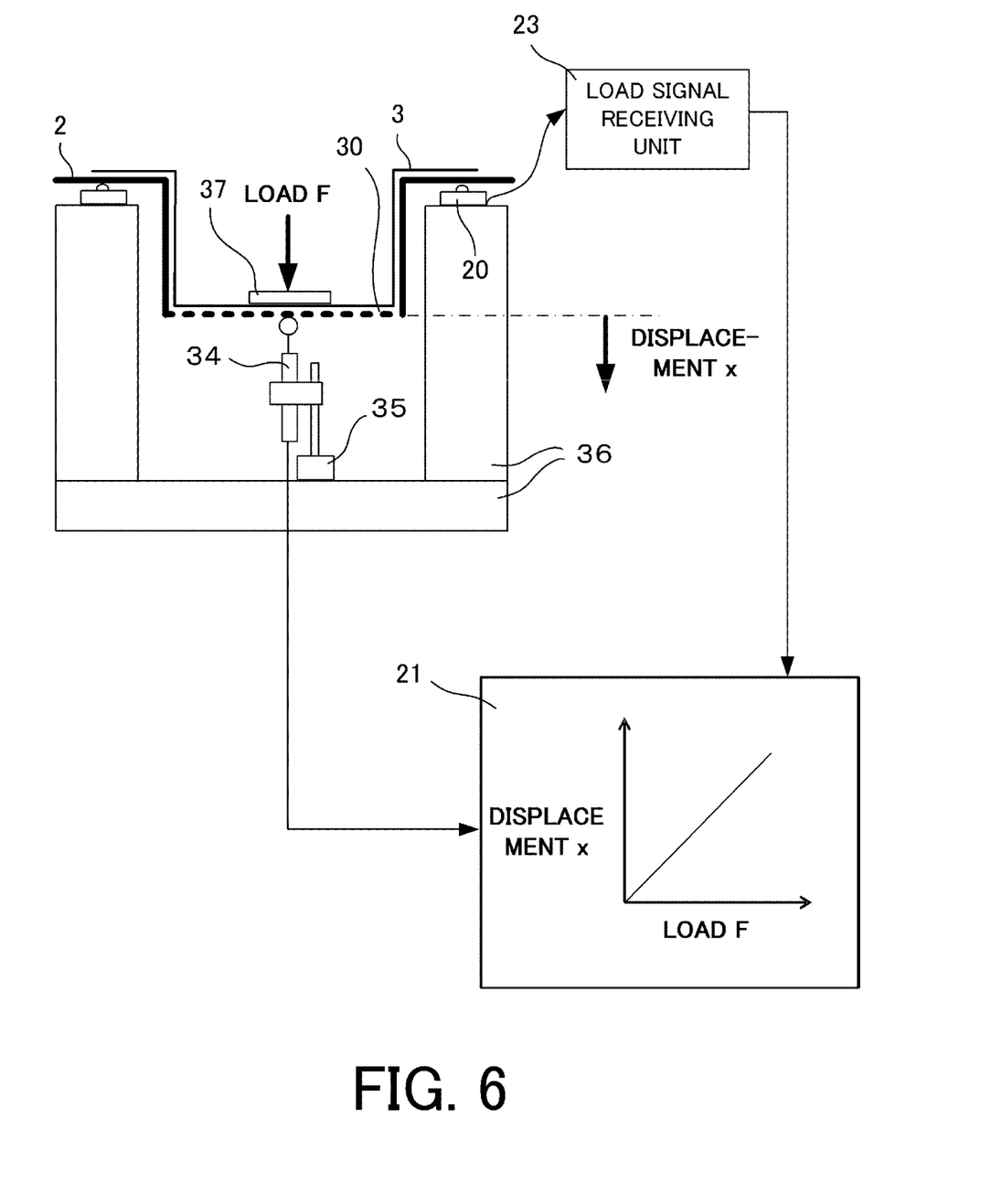
FIG. 6 shows a tool for measuring a relationship of load versus displacement.

An aspect in which the relationship between the load F and the displacement x is obtained from a result of measurement performed by the apparatus 100 which performs photoacoustic measurement is also included in embodiments of the present invention. Alternatively, a dedicated measurement tool may be used separately from the apparatus 100. FIG. 6 shows an example of a tool for measuring a load-to-displacement relationship. The displacement x of the mesh member 30 can be measured by a contact-type displacement sensor 34 fixed to a displacement sensor supporting member 36 by a displacement sensor stand 35. As a displacement sensor, various sensors including a laser displacement meter can be used in addition to a contact-type displacement sensor. Alternatively, an image captured by an optical camera may be analyzed. The load F is applied to a plate 37 simulating an area over which a subject comes into contact with the mesh member 30, and a relationship between a value measured by the load detector 20 and a value of the contact-type displacement sensor 34 is stored in the load-to-displacement memory unit 21. In the present embodiment, the load detecting unit and the load signal receiving unit correspond to the load acquiring unit. In addition, the load F (or a sum value, an average value, or the like thereof) corresponds to the load value.

Figure 7:
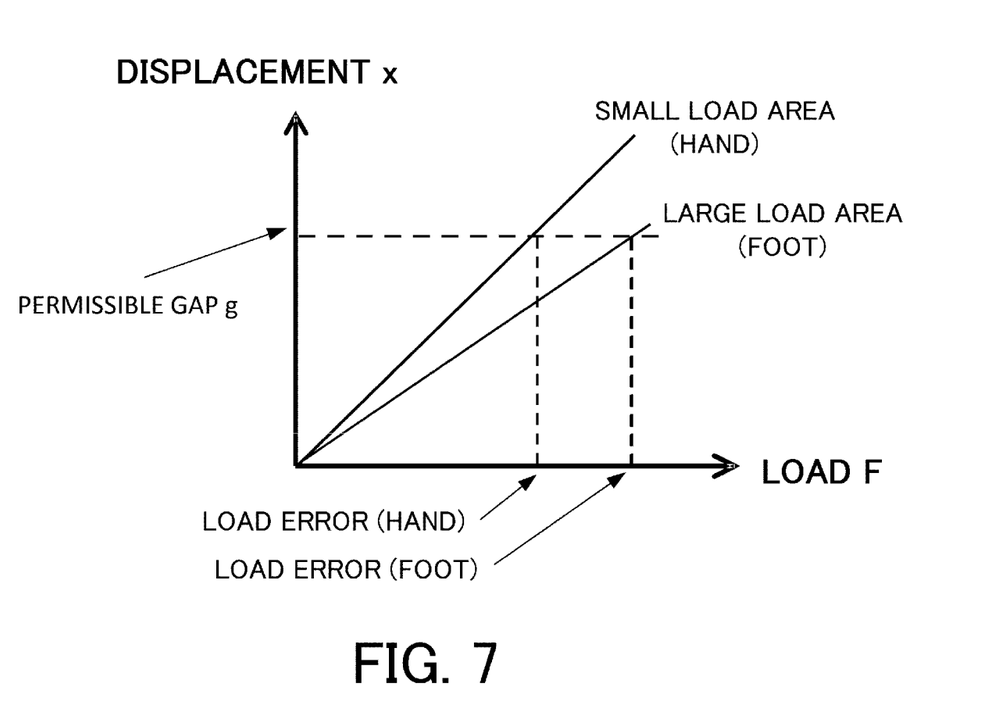
FIG. 7 is a diagram showing a relationship of load versus displacement.

When the subject 4 is a human body part (a hand, a foot, a breast, or the like), a relational expression must be corrected since an area applied with the load with respect to the mesh member 30 may differ. A load value per unit area which is applied to the mesh member 30 will now be considered with reference to the graph shown in FIG. 7. A horizontal axis represents the load F and a vertical axis represents the displacement x. As units thereof, for example, (N) and (cm) may be used or standardized values or apparatus-specific values may be used. A gradient of the graph becomes gradual due to a dispersion of load values in a case of measuring a foot with a large area applied with the load as compared to a case of measuring a hand with a small area applied with the load. In this manner, by setting a relational expression for each of a plurality of measurement portions and using a relational expression by switching among the plurality of relational expressions, an accident due to contact can be prevented in advance and the apparatus can be operated in a safer manner. Moreover, a correction need not necessarily be made when using a method involving directly measuring the displacement x such as image analysis and ultrasound wave reception time measurement.

In addition, a relational expression may be corrected in consideration of a liquid level difference between a liquid level of the acoustic matching liquid 6 in the subject holding member 2 and a liquid level of the acoustic matching liquid 6 in the transducer array 5. In other words, since buoyancy acts on the mesh member 30, the apparatus can be operated in a safer manner by correcting a relational expression in consideration of the liquid level difference. While a relational expression of a load value and a displacement is represented by a graph in FIG. 7, the relationship between the load value and the displacement may be expressed by, for example, a lookup table or an algebraic expression.

Let us now return to FIG. 3. An upper part of the diagram shows the load-to-displacement memory unit 21 for storing a reference value which is defined based on the relationship between the load F and the displacement x and which is used in an apparatus sequence. As the load F corresponding to "displacement x=g (cm)", a "load error reference value Th1

(a first load reference value)" is determined in consideration of a value of the permissible gap g. In addition, in the present embodiment, an "subject presence/absence reference value Th3 (a third load reference value)" which is a load minimally detected when the subject is set to the subject holding member 2 and a "load warning reference value Th2 (a second load reference value)" which is a load representing a possible occurrence of a body motion or the like are defined. These values may be determined in accordance with input values of the user or may be determined based on actual measurements by the apparatus. Values of Th2 and Th3 are smaller than a value of Th1.

In addition, a right side of the lower part of the diagram relates to a structure for setting and determining the reference value. The reference value setting unit 22 sets the reference value to comparators 27 (cT, c1, c2, c3, and c4). A comparison may be performed using a sum value (cT) of the load values or values (c1, c2, c3, and c4) of the load detectors 20 may be respectively compared. By comparing the value of each load detector, even cases where the load value of the subject 4 is not evenly applied to the subject holding member 2 and a load distribution exists can be accommodated.

Results of the comparators 27 are processed by a determining unit 28 and notified to the upper-level control processor 12 via the system bus 13 as a result including a permissible load error. The components shown in FIG. 3 which process load signals and determine reference values may be respectively constituted by a specific processing circuit and so on or may be realized as a functional module of a program which runs on an information processing apparatus.

(Process Flow)

Figure 4:
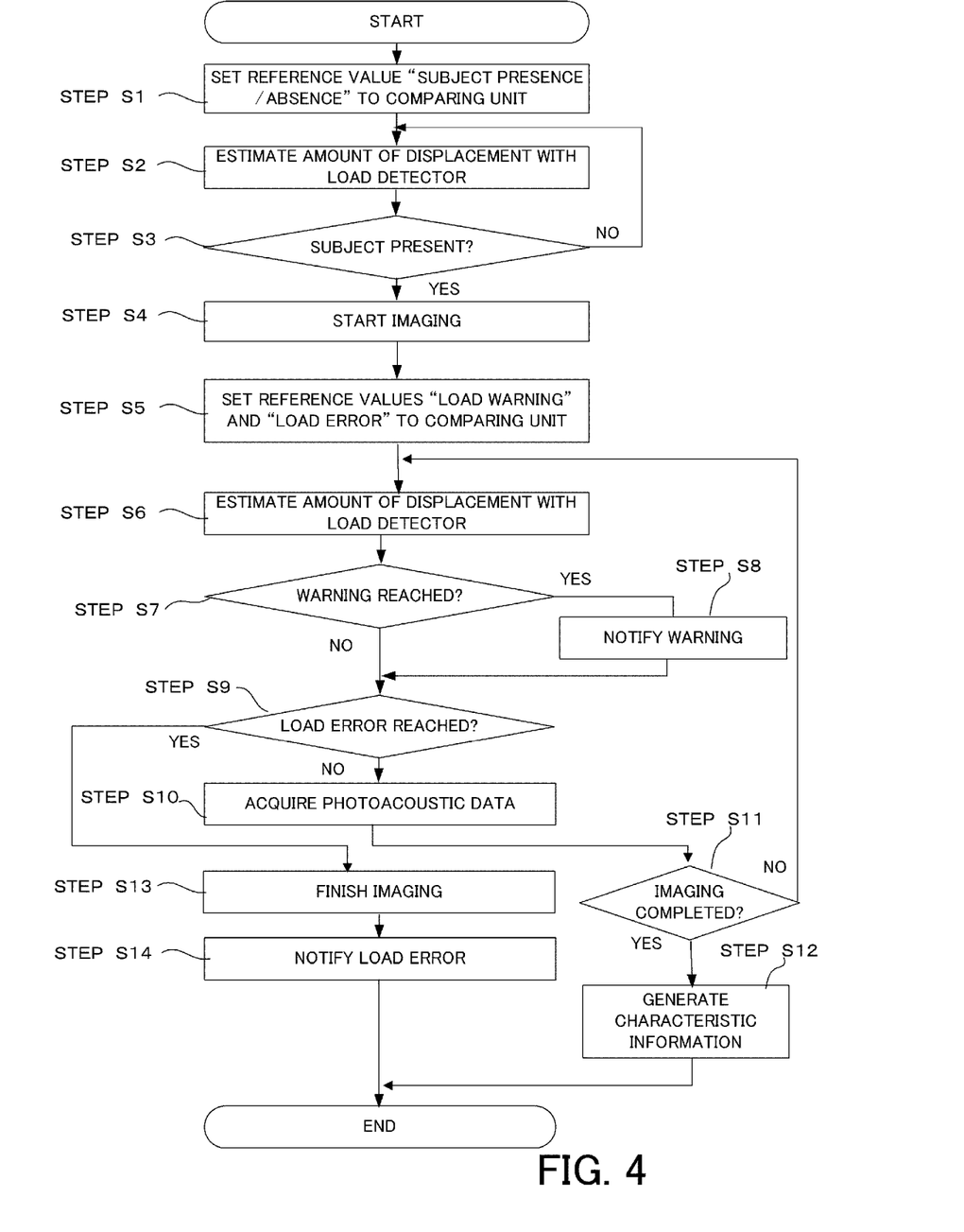
FIG. 4 is a flow chart showing a process by an acoustic wave imaging apparatus.

FIG. 4 shows an example of a flow of an acoustic wave imaging apparatus according to the present embodiment.

(Step S1) The reference value setting unit 22 reads the "subject presence/absence reference value Th3" from the load-to-displacement memory unit 21 and sets the value to the comparator. The present step may be performed in advance before the start of an actual photoacoustic measurement.

(Step S2) Processes of the present step and thereafter are performed in a state where a subject has been set to a prescribed position and a measurement has been started. In the present step, the load signal receiving unit 23 outputs the load F based on a detected value of the load detector 20.

(Step S3) The comparing and determining unit 24 compares the load F acquired by the load detector and the "subject presence/absence reference value Th3". When a subject is present (F>Th3), the flow proceeds to a subsequent process. When a subject is absent (F≤Th3), the flow returns to S2. At this point, the fact that a subject is not set may be presented to the user by sound or a message using a presenting unit constituted by a speaker, a display, or the like.

(Step S4) Imaging is started. When imaging is performed by photoacoustic measurement, an acoustic wave is received in synchronization with light irradiation from the light source and is time-sequentially stored. The photoacoustic measurement may be performed while having the position control mechanism 18 scan the transducers 7.

(Step S5) The reference value setting unit 22 sets the "load warning reference value Th2" and the "load error reference value Th1" to the comparator.

(Step S6) The load signal receiving unit 23 outputs the load F in a similar manner to step S2.

(Step S7) The comparing and determining unit 24 compares the load F acquired by the load detector and the "load warning reference value Th2". When a warning reference is exceeded (F>Th2), the flow proceeds to S8. On the other hand, when the warning reference is not exceeded (F≤Th2), the flow proceeds to S9.

(Step S8) When the reference value "load warning" is reached, the warning is notified to the upper-level control processor and imaging is continued. The control processor presents the warning to the user by sound or a message using a presenting unit constituted by a speaker, a display, or the like.

(Step S9) The comparing and determining unit 24 compares the load F and the "load error reference value Th1". When an error reference is exceeded (F>Th1), the flow proceeds to S11. On the other hand, when the error reference is not exceeded (F≤Th1), the flow proceeds to S10.

(Step S10) Imaging is continued.

(Step S11) In the present step, the control processor determines whether or not imaging has been completed. For example, when a region of interest is set in a subject and imaging is performed by scanning the transducers 7, whether or not imaging has been completed can be determined based on whether or not scanning of the region of interest has been finished. When imaging has not been completed, the flow returns to S6 to acquire a photoacoustic signal from an unmeasured region. On the other hand, the process ends when imaging has been completed.

(Step S12) The image constructing unit 15 performs an image reconstruction process using the acquired photoacoustic signal and generates image data indicating characteristic information inside the subject. The generated image data may be displayed immediately or stored in a memory or the like.

(Step S13) In the present step, imaging is completed.

(Step S14) A "load error" is notified to the upper-level control processor. The control processor performs interlock control including stopping driving in order to ensure safety. Alternatively, the fact that a load error has occurred may be presented to the user by sound or a message using a presenting unit constituted by a speaker, a display, or the like.

In the flow described above, the first load reference value, the second load reference value, and the third load reference value are respectively numerical values which can be compared with the load F (or a value obtained by calculation from outputs of a plurality of load detectors). However, each reference value is not limited to a load value as long as the value is capable of reflecting a deflection of the subject holding member or a displacement of a bottommost point of the subject holding member. For example, when acquiring the displacement x by ultrasound wave echo measurement or an analysis of an optical image, the acquired displacement x may be compared with a reference value determined based on the permissible gap g. Alternatively, after converting a load value into the displacement x using a table or a mathematical expression, the displacement x may be compared with a reference value defined by length. In these cases, a transducer which transmits and receives an acoustic wave, a camera, and an information processing apparatus correspond to the load acquiring unit. In addition, since the displacement x is determined based on an amount of deformation, the displacement x corresponds to the load value.

As described above, with the acoustic wave imaging apparatus according to the present embodiment, a determination is made on whether or not a load value detected by a load cell or the like is within a prescribed permissible range which is defined based on an amount of displacement. In addition, when an error condition set in advance is satisfied, measurement is ended. As a result, even when the load value increases due to a body motion of a subject or the like and a deflection of the subject holding member occurs, effects such as a decline in accuracy of subject information can be reduced.

Second Embodiment

Figure 5:
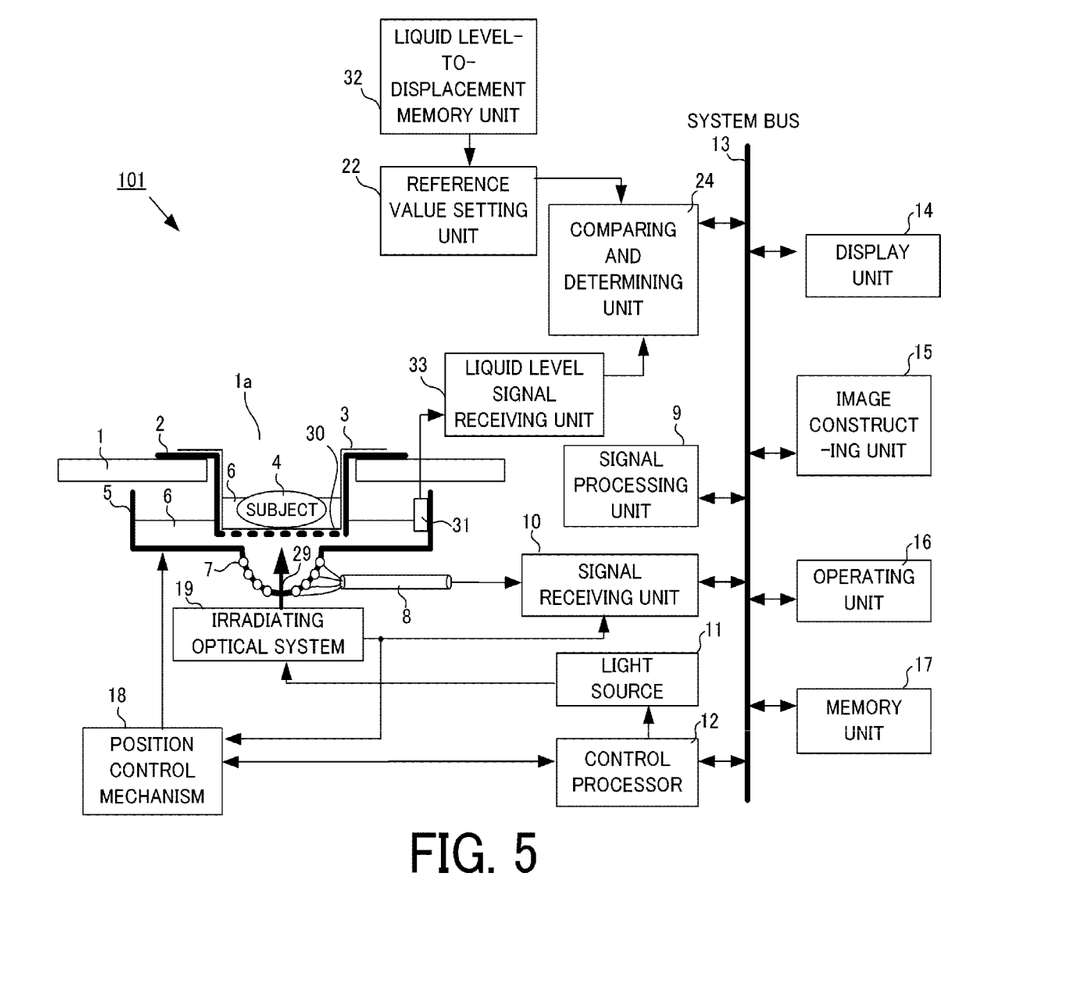
FIG. 5 is a block diagram of an acoustic wave imaging apparatus according to a second embodiment.

FIG. 5 is a block diagram showing an acoustic wave imaging apparatus 101 (hereinafter, simply referred to as the "apparatus 101") according to a second embodiment. Since a basic configuration of the apparatus 101 according to the second embodiment is the same as that of the first embodiment, the following description will focus on differences thereof. The apparatus 101 according to the present embodiment performs control based on a displaced volume of the acoustic matching liquid 6 inside the transducer array due to a deflection of the mesh member 30. The displaced volume corresponds to an amount of deformation of the subject holding member. Specifically, a liquid level sensor 31 for measuring a change in a liquid level of the acoustic matching liquid is provided. In addition, a liquid level signal receiving unit 33 accepts input of a detected value of the liquid level sensor.

A relationship between a displacement of the mesh member 30 and a liquid level of the acoustic matching liquid 6 is obtained in advance and stored in a liquid level-to-displacement memory unit 32. Accordingly, a load value can be estimated based on a liquid level signal that represents an output of the liquid level sensor. In the flow chart shown in FIG. 4, the load detector may be replaced with the liquid level sensor and a reference value based on the load F may be replaced with a reference value based on a liquid level. In this case, the liquid level sensor corresponds to the load acquiring unit and the liquid level corresponds to the load value.

For example, the load error reference value Th1 (the first load reference value) is determined based on a liquid level L1 when the deflection of the mesh equals the permissible gap g. In a similar manner, the load warning reference value Th2 (the second load reference value) and the subject presence/absence reference value Th3 (the third load reference value) are respectively determined based on liquid levels. Alternatively, depending on a form of a container which holds the acoustic matching liquid, determinations may be made based on amounts of leakage instead of liquid levels.

According to the second embodiment, there is no longer a need to measure a load value applied to the subject holding member 2 using a load detector or the like. As a result, the subject holding member 2 can be attached to the supporting member 1 in a simple manner.

Modification

In the second embodiment, when a load error reference value is detected, imaging is aborted by interlock control. However, an operation related to interlock control after the detection of an error is not limited thereto. The present embodiment differs from the second embodiment in that, imaging is temporarily interrupted when a load error reference value is detected and, when a load value is subsequently determined to fall below the load error reference value, interlock control is canceled to restart imaging. In the present embodiment, the fact that a load error has occurred may be presented to the user.

When the acoustic wave imaging apparatus includes a plurality of load detectors 20, in what way an examinee should change his or her posture can be presented by sound or an image based on detected values of the respective load detectors 20. For example, when the plurality of load detectors 20 are arranged so as to surround the subject and a load value corresponding to a right side of the examinee's body is particularly large, the examinee himself or herself instructs a helper to tilt the examinee's body toward a left side. Subsequently, imaging is restarted once output values of the load detectors 20 are confirmed to be under a reference value. An input unit to be used by the examinee or the helper to notify the apparatus that the posture has changed may be provided.

Even when imaging is stopped due to a load error, a photoacoustic signal acquired before the load error is reached may be used to perform image reconstruction of only a portion of a region of interest or may be stored in a memory and subsequently used for image reconstruction in combination with other acquired signals. Alternatively, even when a load error occurs, imaging may be continued and the fact that a photoacoustic signal has been acquired in a state where a load error had occurred may be written into the photoacoustic signal in a format including header information. In this case, favorably, a remark describing the state of occurrence of a load error is also attached to a reconstructed image generated from the photoacoustic signal.

As described above, with the acoustic wave imaging apparatus and the control method thereof according to the respective embodiments, when a deflection of the subject holding member occurs and there is a risk that the subject holding member may come into contact with members including transducers arranged in a periphery of the subject holding member, imaging can be aborted and the apparatus can be stopped. As a result, damage to the respective members due to the deflection of the subject holding member can be prevented in advance.

The present invention can also be implemented by a computer (or a device such as a CPU or an MPU) of a system or an apparatus which realizes functions of the embodiments described above by reading and executing a program recorded on a storage apparatus. In addition, the present invention can also be implemented by a method constituting steps to be executed by computer of a system or an apparatus which realizes functions of the embodiments described above by reading and executing a program recorded on a storage apparatus. Alternatively, the present invention can also be achieved by a circuit (for example, an ASIC) which realizes one or more functions. To this end, for example, the computer is provided with the program via a network or from various types of recording media capable of functioning as the storage apparatus described above (in other words, a computer-readable recording medium which stores data in a non-transitory manner). Therefore, it is to be understood that all of the computer (including a device such as a CPU or an MPU), the method, the program (including a program code or a program product), and the computer-readable recording medium which stores the program in a non-transitory manner described above fall within the scope of the present invention.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-127473, filed on Jun. 28, 2016, which is hereby incorporated by reference herein in its entirety.

What is claimed is:

1. An acoustic wave apparatus comprising:
a supporting member configured to support an examinee, and provided with an insertion opening through which a subject which is a part of the examinee is configured to be inserted;
a subject holding member configured to hold the subject inserted though the insertion opening;
a vessel configured to store an acoustic matching liquid in a certain liquid level to provide acoustic coupling between the subject holding member and the stored acoustic matching liquid;
a transducer array located below the subject holding member and including a plurality of transducers configured to receive acoustic waves from the subject via the subject holding member;
a scanning unit configured to scan the subject by changing a relative position of the transducer array with respect to the subject during a measuring period of time when the acoustic waves are to be received by the transducer array;
a liquid level acquisition unit including a liquid level sensor configured to acquire information corresponding to a liquid level of the stored acoustic matching liquid;
a memory unit configured to store a first liquid level reference value corresponding to a first amount of deformation of the subject holding member when the subject holding member and the transducer array come into contact with each other;
a comparing and determining unit configured to compare the liquid level with the first liquid level reference value and determine whether the scanning is to be aborted or not based on a result of the comparison; and
an interlock controlling unit configured to control the scanning unit to abort the scanning based on the determination of the comparing and determining unit.

2. The acoustic wave apparatus according to claim 1, further comprising:
a load acquiring unit including a plurality of load detectors configured to acquire information corresponding to a plurality of load values applied between the supporting member and the subject holding member corresponding to a plurality of positions.

3. The acoustic wave apparatus according to claim 2, wherein the load acquiring unit is configured to sum the plurality of load values based on the information corresponding to the plurality of load values applied between the supporting member and the subject holding member.

4. The acoustic wave apparatus according to claim 2, further comprising:
a presenting unit configured to present posture information to a user,
wherein the comparing and determining unit is configured to compare among the plurality of load values and determine whether a posture of the examinee is to be changed or not based on the plurality of load values, and
wherein the interlock controlling unit is further configured to control the presenting unit to indicate whether the posture is to be changed or not based on the determination of the comparing and determining unit.

5. The acoustic wave apparatus according to claim 4, wherein the interlock controlling unit is further configured to prevent the subject holding member from contacting the transducer array due to the deformation of the subject holding member.

6. The acoustic wave apparatus according to claim 1, wherein the liquid level acquisition unit is configured to estimate a load value based on the liquid level acquired by the liquid level sensor.

7. The acoustic wave apparatus according to claim 6, further comprising a presenting unit,
wherein the comparing and determining unit is configured to compare the load value with a second liquid level reference value which is smaller than the first liquid level reference value, and
the interlock controlling unit is further configured to cause the presenting unit to output a warning when the comparing and determining unit determines that the load value exceeds the second load reference value.

8. The acoustic wave apparatus according to claim 1, wherein the memory unit is configured to store a relationship between the liquid level and the deformation of the subject holding member as a table or a mathematical expression.

9. The acoustic wave apparatus according to claim 8, wherein the relationship between the liquid level and the deformation of the subject holding member is set to correspond with the pressurized area applied with the load.

10. The acoustic wave apparatus according to claim 1, wherein the interlock controlling unit is configured to cancel the interlock control when, after performing the interlock control, the liquid level falls below the first liquid level reference value.

11. The acoustic wave apparatus according to claim 1, wherein the subject holding member is constituted by a mesh member and a sheet member and is deformable.

12. The acoustic wave apparatus according to claim 1, wherein the transducer array receives a plurality of acoustic waves generated from the subject and outputs a plurality of electrical signals.

13. The acoustic wave apparatus according to claim 12, further comprising an image reconstruction unit configured to generate characteristic information based on the subject using the plurality of electrical signals.

14. The acoustic wave apparatus according to claim 12, further comprising an optical system optically coupled with a light source and configured to irradiate the subject with light from the light source,
wherein the transducer array receives, as the plurality of acoustic waves, a photoacoustic wave generated in response to a light irradiation from the optical system.

15. The acoustic wave apparatus according to claim 14, wherein the interlock controlling unit is further configured to control the light source to stop a light irradiation.

16. The acoustic wave apparatus according to claim 12, wherein the transducer array receives, as the plurality of acoustic waves, a plurality of echo waves which is transmitted from the transducer array and reflected by the subject.

17. The acoustic wave apparatus according to claim 1, wherein the amount of deformation of the subject holding member is corresponding to a load applied to the holding member by the subject.

18. The acoustic wave apparatus according to claim 1, wherein the liquid level corresponds to a position of an interface between the stored acoustic matching liquid and air.

19. An acoustic wave apparatus comprising:
a supporting member configured to support an examinee, and provided with an insertion opening through which a subject which is a part of the examinee is configured to be inserted;
a subject holding member configured to hold the subject inserted though the insertion opening;
a vessel configured to store an acoustic matching liquid in a certain liquid level to provide acoustic coupling between the subject holding member and the stored acoustic matching liquid;
a transducer array located below the subject holding member and including a plurality of transducers configured to receive acoustic waves from the subject via the subject holding member;
a liquid level acquisition unit including a liquid level sensor configured to acquire information corresponding to a liquid level of the stored acoustic matching liquid;
a presenting unit configured to present status information of the subject to a user;
a comparing and determining unit configured to compare the liquid level with a third liquid level reference value and determine whether the subject to be tested is absent or present on the subject holding member; and
an interlock controlling unit configured to control the presenting unit to indicate an absence of the subject to be tested or presence based on a result of the determination of the comparing and determining unit.

20. The acoustic wave apparatus according to claim 19, further comprising:
a memory unit configured to store a first liquid level reference value determined based on the amount of deformation of the subject holding member and a pressurized area applied with a load when the subject holding member and the transducer array come into contact with each other.

21. The acoustic wave apparatus according to claim 20, wherein the interlock controlling unit is further configured to prevent the subject holding member from contacting the transducer array due to the deformation of the subject holding member.

22. The acoustic wave apparatus according to claim 19, wherein the liquid level corresponds to a position of an interface between the stored acoustic matching liquid and air.

23. A method of controlling an acoustic wave apparatus including:
a subject holding member configured to hold a subject which is part of an examinee; a vessel configured to store an acoustic matching liquid; a transducer array including a plurality of transducers located below the subject holding member; and a scanning unit configured to move the transducer array with respect to the subject holding member, the method comprising:
moving the transducer array below the subject holding member, the transducers configured to receive acoustic waves at different positions;
acquiring information corresponding to a liquid level of the acoustic matching liquid stored in the vessel;
comparing the liquid level with a first liquid level reference value corresponding to a first amount of deformation of the subject holding member when the subject holding member and the transducer array come into contact;
determining whether the scanning is to be aborted or not based on a result of the comparison; and
controlling the scanning unit to abort the scanning based on a result of the determination.

24. The method according to claim 23, further comprising:
performing an image reconstruction to generate characteristic information on the subject.

25. The method according to claim 23, wherein the liquid level corresponds to a position of an interface between the stored acoustic matching liquid and air.

* * * * *